United States Patent [19]

Gaa et al.

[11] Patent Number: 5,550,234

[45] Date of Patent: Aug. 27, 1996

[54] POLYALKYLPIPERIDINE COMPOUNDS

[75] Inventors: Karl Gaa, Burtenbach; Matthias Zäh, Gersthofen, both of Germany

[73] Assignee: Hoechst Aktiengesellschaft, Frankfurt am Main, Germany

[21] Appl. No.: 496,496

[22] Filed: Jun. 29, 1995

[30] Foreign Application Priority Data

Jul. 10, 1994 [DE] Germany .................. 44 23 054.0

[51] Int. Cl.⁶ .................. C07D 401/14; C07D 401/06
[52] U.S. Cl. .................. 540/466; 540/543; 540/598; 546/14; 546/19; 544/219; 544/209; 544/212; 544/113; 544/96
[58] Field of Search .................. 544/219, 214, 544/195, 209, 212, 113, 129, 96; 546/14, 18, 19; 540/548, 543, 466

[56] References Cited

U.S. PATENT DOCUMENTS 4,405,735   9/1983   Wiezer et al. .................. 546/19

FOREIGN PATENT DOCUMENTS

| 0008102 | 9/1981 | European Pat. Off. . |
| 0057885 | 8/1982 | European Pat. Off. . |
| 0028318 | 12/1982 | European Pat. Off. . |
| 0208263 | 9/1989 | European Pat. Off. . |

*Primary Examiner*—John M. Ford
*Attorney, Agent, or Firm*—Connolly & Hutz

[57] ABSTRACT

Polyalkylpiperidine compounds of the formula I

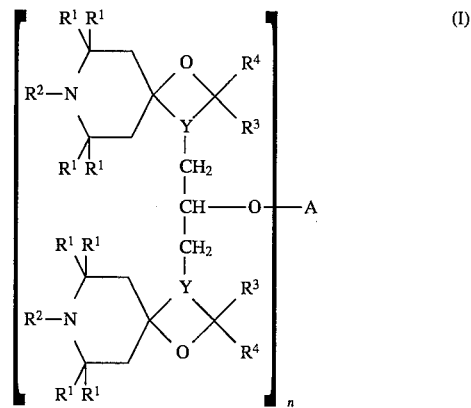

in which Y is one of the groups

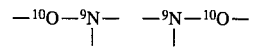

are distinguished by very low volatility at elevated temperature and are very effective stabilizers for organic substances.

3 Claims, No Drawings

POLYALKYLPIPERIDINE COMPOUNDS

The present invention relates to novel polyalkylpiperidine compounds which are distinguished by particularly low volatility at elevated temperature.

It is known that organic compounds are damaged by light, radiation, oxygen or heat. There have already been many publications describing compounds for stabilizing organic material. Some of them relate to compounds based on 2,2,6,6-tetramethylpiperidine. Specific spiro compounds have proven particularly effective (cf. EP 8 102, EP 28 318 and EP 280 263).

Also known are diazaspirodecanes of the formula

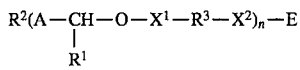

in which $R^1$ is a diazaspirodecyl group (cf. EP 57 885). These compounds have been found to have the disadvantage of being relatively volatile at elevated temperature.

Surprisingly, it has been found that compounds having a similar structure have significantly lower volatility.

The invention thus relates to compounds of the formula I

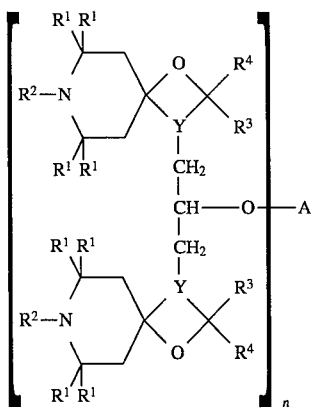

in which Y is the group

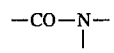

$R^1$ is a hydrogen atom or an alkyl group, $R^2$ is a hydrogen atom or an alkyl group, $R^3$ and $R^4$ are identical or different and are a hydrogen atom or an alkyl group, or $R^3$ and $R^4$, together with the carbon atom connecting them, form a ring having 5 to 12 ring members, n is 1, 2 or 3, and A, in the case where n=1, is —COOR$^5$, —P(OR$^6$)(OR$^7$), —Si(OR$^5$)(OR$^5$)(OR$^5$), —SiR$^5$R$^5$R$^5$ or the

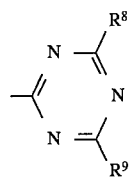

group,

A, in the case where n=2, is —CO—, =POR$^5$, =Si(OR$^5$)(OR$^5$), =SiR$^5$R$^5$ or the

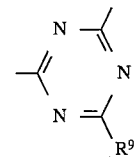

group,

A, in the case where n=3, is ≡Si(OR$^5$), ≡SiR$^5$ or the

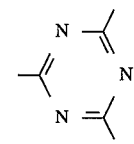

group, $R^5$ is a $C_1$–$C_{18}$-alkyl group, a $C_2$–$C_{18}$-alkenyl group, a $C_2$–$C_{18}$-alkynyl group, a $C_5$–$C_{12}$-cycloalkyl group, a $C_6$–$C_{10}$-bicycloalkyl group, a $C_7$–$C_8$-cycloalkenyl group, a $C_6$–$C_{10}$-aryl group, a $C_7$–$C_9$-aralkyl group, a $C_7$–$C_9$-alkaryl group, unsubstituted or substituted by $C_1$–C4-alkyl or phenyl, where a plurality of radicals $R^5$ may be identical or different, $R^6$ and $R^7$ are identical or different and are a $C_1$–$C_{18}$-alkyl group, a $C_2$–$C_{18}$-alkenyl group, a $C_2$–$C_{18}$-alkynyl group, a $C_5$–$C_{12}$-cycloalkyl group, a $C_6$–$C_{10}$-bicycloalkyl group, a $C_5$–$C_8$-cycloalkenyl group, a $C_6$–$C_{10}$aryl group, a $C_7$–$C_9$-aralkyl group or a $C_7$–$C_9$-aralkyl group, substituted by $C_1$–$C_4$-alkyl or phenyl, or are a radical of the formula II or III

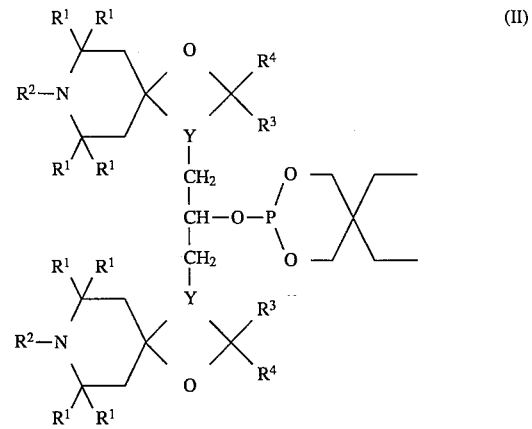

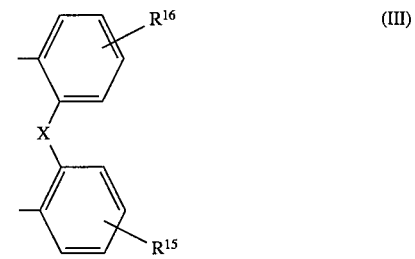

in which $R^1$, $R^2$, $R^3$, $R^4$ and $R^5$ are as defined above, and X is a direct bond or methylene group or a 1,1-alkylidene group having 2 to 5 carbon atoms, $R^8$ and $R^9$ are identical or different and are —OR$^5$, —NHR$^5$, —NR$^{11}$R$^{12}$ or one of the two groups

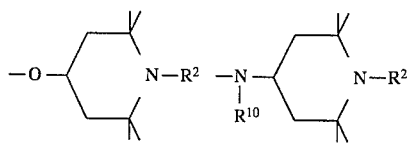

in which $R^{10}$ is a hydrogen atom, a $C_1-C_{12}$-alkyl group, a $C_5-C_7$-cycloalkyl group, a $C_7-C_9$-aralkyl group, a $C_8-C_{18}$-alkanoyl group, a $C_3-C_5$-alkenoyl group or a benzoyl group, or is

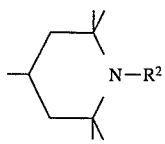

$R^{11}$ and $R^{12}$ are identical or different and are a $C_1-C_{10}$-alkyl group, a $C_5-C_7$-cycloalkyl group or a $C_6-C_{10}$-aryl group, or $R^{11}$ and $R^{12}$, together with the nitrogen, form a 5- to 12-membered ring, which may also contain oxygen.

The invention also relates to the preparation of these compounds and to their use for stabilizing organic material, in particular plastics, oils and surface coatings.

In the formula I

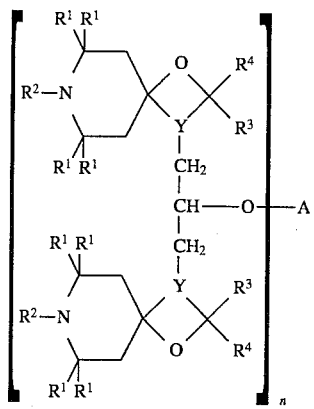

Y is the group

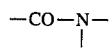

where the numbers shown indicate the position of the atoms in the spirodecyl five-membered ring. Y is preferably a group in which the oxygen atom is adjacent to the carbon atom common to both rings, i.e.

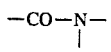

n is 1, 2 or 3, preferably 1.

$R^1$ is a hydrogen atom or a $C_1-C_4$-alkyl group, preferably a methyl group.

$R^2$ is a hydrogen atom or a $C_1-C_{12}$-alkyl group, preferably a methyl group.

$R^3$ and $R^4$ are identical or different and are a hydrogen atom, a $C_1-C_8$-, preferably $C_1-C_4$-alkyl group, or $R^3$ and $R^4$, together with the carbon atom connecting them, form a ring having 5 to 12, preferably 6 or 12, ring members. Preferably $R^3$ and $R^4$ are methyl, a six-membered ring or a twelve-membered ring.

$R^5$ is a $C_1-C_{18}$-, preferably $C_1-C_8$-alkyl group, a $C_2-C_{18}$-, preferably $C_3-C_6$-alkenyl group, a $C_2-C_{18}$-, preferably $C_2-C_8$-alkynyl group, a $C_5-C_{12}$-, preferably $C_5-C_6$-cycloalkyl group, a $C_6-C_{10}$-, preferably $C_6-C_{10}$-bicycloalkyl group, a $C_5-C_8$-, preferably $C_5-C_6$-cycloalkenyl group, a $C_6-C_{10}$-, preferably $C_6$- or $C_{10}$-aryl group, a $C_7-C_9$-aralkyl group, a $C_7-C_9$-aralkyl group, substituted by $C_1-C_4$-alkyl or phenyl, where a plurality of radicals $R^5$ may be identical or different.

If n=1, A is a —COOR$^5$, —P(OR$^6$) (OR$^7$), —Si(OR$^5$) (OR$^5$) (OR$^5$) or —SiR$^5$R$^5$R$^5$ group, in which $R^5$ is as defined above.

$R^6$ and $R^7$ are identical or different and are a $C_1-C_{18}$-, preferably $C_1-C_8$-alkyl group, a $C_2-C_{18}$-, preferably $C_3-C_6$-alkenyl group, a $C_2-C_{18}$-, preferably $C_2-C_8$-alkynyl group, a $C_5-C_{12}$-, preferably $C_5-C_6$-cycloalkyl group, a $C_6-C_{10}$-, preferably $C_8-C_{10}$-bicycloalkyl group, a $C_5-C_8$-, preferably $C_5-C_6$-cycloalkenyl group, a $C_6-C_{10}$-, preferably $C_6$- or $C_{10}$-aryl group, a $C_7-C_9$-aralkyl group or a $C_7-C_9$-aralkyl group, substituted by $C_1-C_4$-alkyl or phenyl, or are a radical of the formula II or III

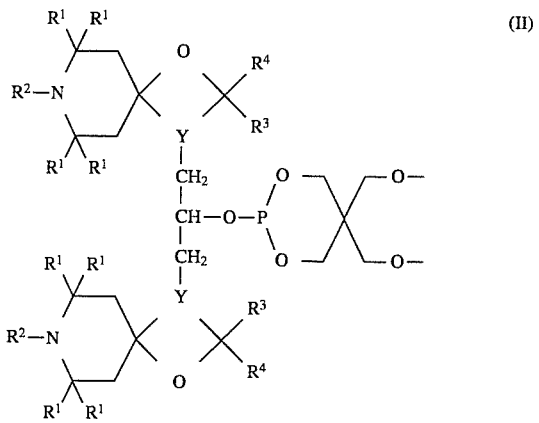

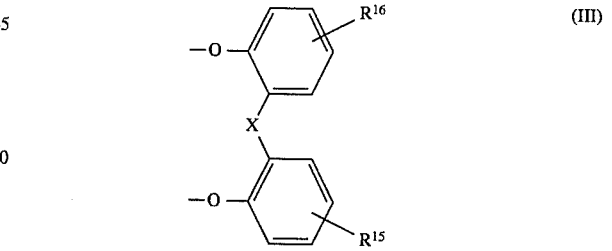

in which $R^1$, $R^2$, $R^3$, $R^4$ and $R^5$ are as defined above, and X is a direct bond or a methylene group or a 1,1-alkylidene group having 2 to 5 carbon atoms, or A is

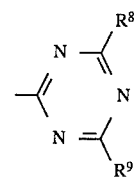

in which $R^8$ and $R^9$ are identical or different and are —OR$^5$, —NHR$^5$, —NR$^{11}$R$^{12}$ or one of the two groups

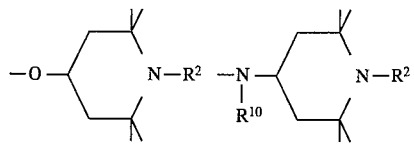

in which $R^{10}$ is a hydrogen atom, a $C_1-C_{12}$-, preferably $C_1-C_8$-alkyl group, a $C_5-C_7$-, preferably $C_5-C_6$-cycloalkyl group, a $C_7-C_9$-aralkyl group, a $C_8-C_{18}$-, preferably $C_2-C_8$-alkanoyl group, a $C_3-C_5$-, preferably $C_3-C_4$-alkenoyl group or a benzoyl group, or is

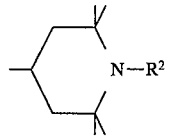

$R^{11}$ and $R^{12}$ are identical or different and are a $C_1-C_{18}$-, preferably $C_1-C_8$-alkyl group, a $C_5-C_7$-cycloalkyl group, a $C_6-C_{10}$-, preferably $C_6$-aryl group, or $R^{11}$ and $R^{12}$, together with the nitrogen, form a 5- to 12-, preferably 5- to 6-membered ring, which may also contain oxygen, in particular a pyrrolidine, piperidine or morpholine ring.

A is preferably $-Si(CH_3)_3$, $-COO$-alkyl or

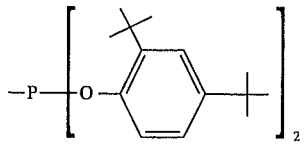

If n=2, A is $-CO-$, $=POR^5$, $=Si(OR^5)$ $(OR^5)$, $=SiR^5R^5$ or the

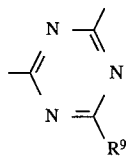

group, in which $R^5$ and $R^9$ are as defined above.

A is preferably $-CO-$, $-Si(CH_3)_3$,

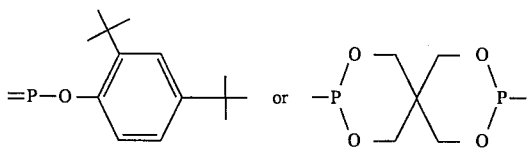

If n=3, A is $=Si(OR^5)$, $=SIR^5$ or the

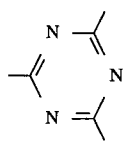

group, where $R^5$ is as defined above.

A is preferably

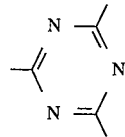

The compounds of the formula I in which A is not H can advantageously be prepared by reactions, known per se, of the alcohols of the formula IV

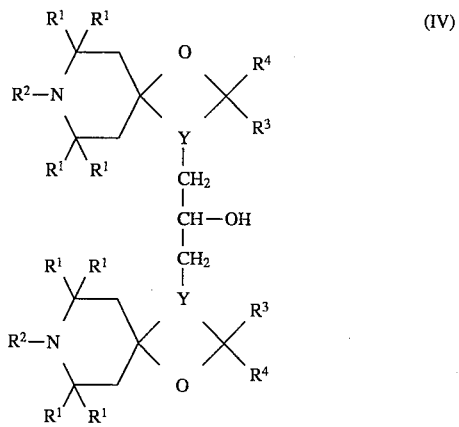

with the corresponding reactive components of the formula V $$A+Z]_n \qquad (V)$$

where

Z is a halogen atom or the $=OR^5$ group for $A=-CO-$, $-COOR^5$, $-P(OR^6)$ $(OR^7)$ or $=POR^5$;

Z is a halogen atom for $A=-Si(OR^5)$ $(OR^5)$ $(OR^5)$, $-SiR^5R^5R^5$, $=Si(OR^5)$ $(OR^5)$, $=SiR^5R^5$, $=Si(OR^5)$, $=SiR^5$ or a triazine derivative.

$R^5$, $R^6$ and $R^7$ are as defined above.

Another method of preparing the novel compounds of the formula I in which $R^2$=alkyl comprises reacting the compounds I in which $R^2$=H with the conventional reagents to give the substituted products I in which $R^2$=alkyl.

The reaction is carried out in a protic or aprotic, organic solvent, preferably a hydrocarbon, in particular an aromatic hydrocarbon, such as, for example, toluene or xylene, or in mixtures thereof or in an alcohol, preferably an aliphatic alcohol, in particular in a $C_1-C_{12}$-alcohol, such as in isopropanol or in a mixture of a hydrocarbon and an alcohol, in particular xylene or isopropanol. Another possibility is to use one of the reaction components in excess as solvent.

The reaction is carried out in the presence of bases. Molar amounts of base are employed, even catalytic amounts being sufficient for transesterification reactions.

The reaction is carried out at a temperature of from 20° C. to the boiling point of the solvent; the suitable temperature depends on the base used and on the reactivity of the compound of the formula V employed.

The novel compounds of the formula I can be in the form of the free bases or as acid-addition salts. Suitable anions are derived, for example, from inorganic acids and in particular from organic acids or sulfonic acids. Examples of inorganic anions are chloride, bromide, sulfate, tetrafluoroborate, phosphate and rhodanide. Suitable carboxylic acids are formate, acetate, propionate, hexanoate, cyclohexanoate, lactate, stearate, acrylate, methacrylate, citrate, malonate and succinate, and anions of polycarboxylic acids containing up to 3000 COOH groups. Examples of sulfonic acid anions are benzenesulfonate and tosylate.

The novel compounds are highly suitable for stabilizing organic material against the action of light, oxygen and heat. They are added to the organic material to be stabilized in a concentration of from 0,001 to 5% by weight, preferably from 0.02 to 1% by weight, based on the organic material, before, during or after its preparation.

The term organic material is taken to mean, for example, precursors for plastics, surface coatings and oils, in particular plastics, surface coatings and oils themselves.

The present invention also relates to organic material, in particular plastics, surface coatings and oils, which has been stabilized against the action of light, oxygen and heat and which contains the compound in the above-mentioned concentrations. These organic materials include the following substances:

1. Polymers of mono- and diolefins, for example high-, medium- or low-density polyethylene (which may have been crosslinked), polypropylene, polyisobutylene, poly-1-butene, polymethyl-1-pentene, polyisoprene or polybutadiene, and polymers of cycloolefins, such as, for example, of cyclopentene or norbornene.
2. Mixtures of the polymers mentioned under 1), for example mixtures of polypropylene with polyethylene or with polyisobutylene.
3. Copolymers of mono- and diolefins with one another or with other vinyl monomers, such as, for example, ethylene-propylene copolymers, propylene-1-butene copolymers, propylene-isobutylene copolymers, ethylene-1-butene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers, and salts thereof (ionomers), and terpolymers of ethylene with propylene and a diene, such as hexadiene, dicyclopentadiene or ethylidenenorbornene.
4. Polystyrene and poly (p-methylstyrene).
5. Copolymers of styrene or α-methylstyrene with dienes or acrylic derivatives, such as, for example, styrene-butadiene, styrene-maleic anhydride, styrene-acrylonitrile, styrene-ethyl methacrylate, styrene-butadiene-ethyl acrylate, styrene-acrylonitrilemethacrylate; high-impact-strength mixtures of styrene copolymers and another polymer, such as, for example, a polyacrylate, a diene polymer or an ethylene-propylenediene terpolymer; and block copolymers of styrene, such as, for example, styrene-butadiene-styrene, styrene-isoprene-styrene, styrene-ethylene/butylene-styrene or styrene-ethylene/propylene-styrene.
6. Graft copolymers of styrene, such as, for example, styrene on polybutadiene, styrene and acrylonitrile on polybutadiene, styrene and maleic anhydride on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and mixtures thereof with the copolymers mentioned under 5), which are known, for example, as ABS, MBS, ASA or AES polymers.
7. Polyvinyl chloride.
8. Copolymers of vinyl chloride, which can be prepared by known processes (for example suspension, bulk or emulsion polymerization).
9. Copolymers of vinyl chloride containing up to 30% by weight of comonomers, such as, for example, vinyl acetate, vinylidene chloride, vinyl ethers, acrylonitrile, acrylates, maleic monoesters or diesters or olefins, and graft polymers of vinyl chloride.
10. Halogen-containing polymers, such as, for example, polychloroprene, chlorinated rubber, chlorinated or chlorosulfonated polyethylene, epichlorohydrin homopolymers and copolymers, in particular polymers of halogen-containing vinyl compounds, such as, for example, polyvinylidene chloride, polyvinyl fluoride, polyvinylidene fluoride; and copolymers thereof, such as of vinyl chloride-vinylidene chloride, vinyl chloride-vinyl acetate or vinylidene chloride-vinyl acetate.
11. Polymers derived from α,β-unsaturated acids and derivatives thereof, such as polyacrylates and polymethacrylates, polyacrylamides and polyacrylonitriles.
12. Copolymers of the monomers mentioned under 11) with one another or with other unsaturated monomers, such as, for example, acrylonitrile-butadiene copolymers, acrylonitrile-alkyl acrylate copolymers, acrylonitrile-alkoxyacrylate copolymers, acrylonitrile-vinyl halide copolymers or acrylonitrile-alkyl methacrylate-butadiene copolymers.
13. Polymers derived from unsaturated alcohols and amines or acyl derivatives or acetals thereof, such as polyvinyl alcohol, polyvinyl acetate, stearate, benzoate or maleate, polyvinylbutyral, polyallylphthalate and polyallylmelamine.
14. Homopolymers and copolymers of cyclic ethers, such as polyethylene glycols, polyethylene oxide, polypropylene oxide or copolymers thereof with bisglycidyl ethers.
15. Polyacetals, such as polyoxymethylene, and polyoxymethylenes containing comonomers, such as, for example, ethylene oxide.
16. Polyphenylene oxides and sulfides, and mixtures thereof with styrene polymers.
17. Polyurethanes derived from polyethers, polyesters and polybutadienes containing terminal hydroxyl groups on the one hand and aliphatic or aromatic polyisocyanates on the other hand, and precursors thereof (polyisocyanate-polyol prepolymers).
18. Polyamides and copolyamides derived from diamines and dicarboxylic acids and/or from aminocarboxylic acids or the corresponding lactams, such as nylon 4, nylon 6, nylon 6.6, nylon 6.10, nylon 11, nylon 12, poly-2,4,4-trimethylhexamethyleneterephthalamide, poly-m-phenyleneisophthalamide, and copolymers thereof with polyethers, such as, for example, with polyethylene glycol, polypropylene glycol or polytetramethylene glycol.
19. Polyureas, polyimides and polyamide imides.
20. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly(2,2-bis(4-hydroxyphenyl)propane) terephthalate, polyhydroxybenzoates, and a block polyether-ester derived from polyethylene containing hydroxyl terminal groups, dialcohols and dicarboxylic acids.
21. Polycarbonates and polyester carbonates.
22. Polysulfones, polyether sulfones and polyether ketones.
23. Crosslinked polymers derived from aldehydes on the one hand and phenols, urea or melamine on the other hand, such as phenol-formaldehyde, urea-formaldehyde and melamine-formaldehyde resins.
24. Drying and non-drying alkyd resins.

25. Unsaturated polyester resins derived from copolyesters of saturated and unsaturated dicarboxylic acids with polyhydric alcohols, and vinyl compounds as crosslinking agents, and also halogen-containing, low-combustibility modifications thereof.
26. Crosslinkable acrylic resins derived from substituted acrylates, such as, for example, epoxy acrylates, urethane acrylates or polyester acrylates.
27. Alkyd resins, polyester resins and acrylate resins which have been crosslinked with melamine resins, urea resins, polyisocyanates or epoxy resins.
28. Crosslinkable epoxy resins derived from polyepoxides, for example from bis-glycidyl ethers or from cycloaliphatic diepoxides.
29. Natural polymers, such as cellulose, natural rubber, gelatin or derivatives thereof which have been chemically modified in a polymer-homologous reaction, such as cellulose acetates, propionates and butyrates, or cellulose ethers, such as methyl cellulose.
30. Mixtures of the abovementioned polymers, such as, for example, PP/EPDM, nylon 6/EPDM or ABS, PVC/EVA, PVC/ABS, PVC/MBS, PC/ABS, PBTP/ABS, PC/ASA, PC/PBT, PVC/CPE, PVD/acrylate, POM/thermoplastic PUR, POM/acrylate, POM/MBS, PPE/HIPS, PPE/nylon 6.6 and copolymers, PA/HDPE, PA/PP and PA/PPE.
31. Naturally occurring and synthetic organic substances which are pure monomers or mixtures of monomers, such as, for example, mineral oils, animal and vegetable fats, oils and waxes, or oils, fats and waxes based on synthetic esters, or mixtures of these substances.
32. Aqueous dispersions of natural or synthetic rubber.

The novel compounds are preferably used to stabilize polyolefins, such as polyethylene and polypropylene.

The organic material stabilized by means of the novel compounds can, if desired, also contain further additives, for example antioxidants, light stabilizers, metal deactivators, antistatic agents, flame proofing agents, pigments and fillers.

Antioxidants and light stabilizers which can be added in addition to the novel compounds are, for example, compounds based on sterically hindered amines or sterically hindered phenols or sulfur- or phosphorus-containing costabilizers.

Examples of suitable compounds of this type are:

1 Antioxidants 1.1 Alkylated monophenols, for example 2,6-di-t-butyl-4-methylphenol, 2-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures of these compounds 1.2 Alkylthiomethylphenols, for example 2,4-dioctylthiomethyl-6-t-butylphenol, 2,4-dioctylthiomethyl-6-methylphenol, 2,4-dioctylthiomethyl-6-ethylphenol, 2,6-di-dodecylthiomethyl-4-nonylphenol.

1.3 Hydroquinones and alkylated hydroquinones, for example 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyanisole, 3,5-di-t-butyl-4-hydroxyphenyl stearate, bis(3,5-di-t-butyl-4-hydroxyphenyl) adipate.

1.4 Hydroxylated thiodiphenyl ethers, for example 2,2'-thiobis(6-t-butyl-4-methylphenol), 2,2'-thiobis (4-octyl-phenol), 4,4'-thiobis(6-t-butyl-3-methylphenol), 4,4'-thiobis(6-t-butyl-2-methylphenol), 4,4'-thiobis (3,6-di-sec-amylphenol), 4,4'-bis(2,6-dimethyl-4-hydroxyphenyl) disulfide.

1.5 Alkylidenebisphenols, for example 2,2'-methylenebis(6-t-butyl-4-methylphenol), 2,2'-methylenebis(6-t-butyl-4-ethylphenol), 2,2'-methylenebis[4-methyl-6-(αmethylcyclohexyl)phenol], 2,2'-methylenebis (4-methyl-6-cyclohexylphenol), 2,2'-methylenebis (6-nonyl-4-methylphenol), 2,2'-methylenebis(4,6-di-t-butylphenol), 2,2'-ethylidenebis (4,6-di-t-butylphenol), 2,2'-ethylidenebis (6-t-butyl -4-isobutylphenol), 2,2'-methylenebis[6-(α-methylbenzyl)-4-nonylphenol], 2,2'-methylenebis [6-(α,α-dimethylbenzyl)-4-nonylphenol], 4,4'-methylenebis (2,6-di-t-butylphenol ), 4,4'-methylenebis(6-t-butyl -2-methylphenol), 1,1-bis(5-t-butyl-4-hydroxy-2-methylphenyl)-butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis(3-t-butyl-4-hydroxy-5-methyl-phenyl)dicyclopentadiene, bis[2-(3'-t-butyl-2'-hydroxy-5'-methylbenzyl) -6-t-butyl-4-methylphenyl]terephthalate, 1,1-bis(3,5-dimethyl-2-hydroxyphenyl)butane, 2,2-bis(3,5-di-t-butyl-4-hydroxyphenyl)-propane, 2,2-bis(5-t-butyl-4-hydroxy-2-methylphenyl)-4-n-dodecylmercaptobutane, 1,1, 5,5-tetra-(5-t-butyl-4-hydroxy-2-methylphenyl)pentane.

1.6 O—, N— and S-benzyl compounds, for example 3,5,3'5'-tetra-t-butyl-4,4'-dihydroxydibenzyl ether, octadecyl 4-hydroxy-3,5-dimethylbenzylmercaptoacetate, tris(3,5-di-t-butyl-4-hydroxybenzyl)amine, bis(4-t-butyl-3-hydroxy-2,6-dimethylbenzyl) dithioterephthalate, bis(3,5-di-t-butyl-4-hydroxybenzyl) sulfide, isooctyl 3,5-di-t-butyl-4-hydroxybenzylmercaptoacetate.

1.7 Hydroxybenzylated malonates, for example dioctadecyl-2,2-bis(3,5-di-t-butyl -2-hydroxybenzyl)-malonate, dioctadecyl 2-(3-t-butyl-4-hydroxy -5-methylbenzyl)malonate, didodecylmercaptoethyl 2,2-bis(3,5-di-t-butyl-4-hydroxybenzyl)malonate.

1.8 Aromatic hydroxybenzyl compounds, for example 1,3,5-tris (3,5-di -t-butyl-4-hydroxybenzyl)-2,4,6-trimethyl benzene, 1,4-bis (3,5-di-t-butyl-4-hydroxybenzyl)-2,3,5,6-tetramethylbenzene, 2,4,6-tris(3,5-di-t-butyl-4-hydroxybenzyl)phenol.

1.9 Triazine compounds, for example 2,4-bis(octyl mercapto)-6 6-(3,5-di-t-butyl-4-hydroxyanilino)-1,3,5-triazine, 2-octylmercapto-4,6-bis(3,5-di-t-butyl-4-hydroxyanilino)-1,3,5-triazine, 2-octylmercapto -4,6-bis(3,5-di-t-butyl-4-hydroxyphenoxy) -1,3,5-triazine, 2,4,6-tris(3,5-di-t-butyl-4-hydroxyphenoxy)-1,2,3-triazine 1,3,5-tris(3,5-t-butyl-4-hydroxybenzyl) isocyanurate, 1,3,5- tris(4-t-butyl-3-hydroxy-2,6-dimethylbenzyl) isocyanurate, 2,4,6-tris(3,5-di-t-butyl- 4-hydroxyphenylethyl)-1,3,5-triazine, 1,3,5-tris(3,5-di-t-butyl- 4-hydroxyphenylpropionyl)-hexahydro-1,3,5-triazine, 1,3,5-tris (3,5-dicyclohexyl-4-hydroxybenzyl)isocyanurate.

1.10 Benzylphosphonates, for example dimethyl 2,5-di-t-butyl-4-hydroxybenzylphosphonate, diethyl 3,5-di-t-butyl-4-hydroxybenzylphosphonate, dioctadecyl3,5-di-t-butyl-4-hydroxybenzylphosphonate, dioctadecyl 5-t-butyl-4-hydroxy-3-methylbenzyl-phosphonate, calcium ethyl3,5-di-t-butyl-4-hydroxybenzylphosphonate.

1.11 Acylaminophenols, for example 4-hydroxylauranilide, 4-hydroxystearanilide, octyl N-(3,5-di-t-butyl-4-hydroxyphenyl) carbamate.

1.12 Esters of β-(3,5-di-t-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13 Esters of β-(5-t-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-t-butyl-4-hydroxyphenylacetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N0'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo [2.2.2]-octane.

1.16 Esters of 3,3-bis(3'-t-butyl-4'-hydroxyphenyl)butyric acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17 Amides of β-(3,5-di-t-butyl-4-hydroxyphenyl)-propionic acid, e.g. N,N'-bis(3,5-di-t-butyl-4-hydroxyphenylpropionyl)hexamethylenediamine, N,N'-bis(3,5-di-t-butyl-4-hydroxyphenylpropionyl)trimethylenediamine, N,N'-bis(3,5-di-t-butyl-4-hydroxyphenylpropionyl)hydrazine.

2 UV absorbers and light stabilizers 2.1 2-(2'-Hydroxyphenyl)benzotriazoles, for example 2-(2'-hydroxy-5'-methylphenyl)benzotriazole, 2-(3',5'-di-t-butyl-2'-hydroxyphenyl)benzotriazole, 2-(5'-t-butyl-2'hydroxyphenyl)benzotriazole, 2-[2'-hydroxy-5'-(1,1,3,3-tetramethylbutyl)phenyl]benzotriazole, 2-(3',5'-di-t-butyl-2'-hydroxyphenyl)-5-chlorobenzotriazole, 2-( 3'-t-butyl-2'-hydroxy-5'-methylphenyl)-5-chlorobenzotriazole, 2-(3'-sec-butyl-5'-t-butyl-2'-hydroxyphenyl) benzotriazole, 2-(2'-hydroxy-4'-octyloxyphenyl)benzotriazole, 2-(3',5'-di-t-amyl-2'-hydroxyphenyl) benzotriazole, 2-(3',5'-bis(α,α-dimethylbenzyl)-2'-hydroxyphenyl) benzotriazole, mixture of 2-(3'-t-butyl-2'-hydroxy-5'-( 2-octyloxycarbonylethyl)-5-chlorobenzotriazole, 2-( 3'-t-butyl -5'-[2-(2-ethylhexyloxy-)carbonyl ethyl]-2'-hydroxy-phenyl)-5-chlorobenzotriazole, 2-(3'-t-butyl -2'-hydroxy-5'-(2- methoxycarbonyl ethyl) phenyl)-5-chlorobenzotriazole, 2-(3'-t-butyl-2'-hydroxy-5'-(2-methoxycarbonylethyl)-phenyl)benzotriazole, 2-(3'-t-butyl-2'-hydroxy-5'-(2-octyloxycarbonylethyl)phenyl)benzotriazole, 2-(3'-t-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-t-butyl-2'-hydroxy-5'-(2-isooctyloxycarbonylethyl)phenyl)benzotriazole, 2,2'-methylenebis [4-(1,1,3,3-tetramethylbutyl)-6-benzotriazole-2-yl-phenol]; the transesterification product of 2-[3'-t-butyl-5'-(2-methoxycarbonyl ethyl)-2'- hydroxyphenyl]benzotriazole with polyethylene glycol 300.

2.2 2-Hydroxybenzophenones, for example the 4-hydroxy, 4-methoxy, 4-octyloxy, 4-decyloxy, 4-dodecyloxy, 4-benzyloxy, 4,2'4'-trihydroxy and 2'-hydroxy 4,4'-di methoxy derivatives.

2.3 Esters of substituted and unsubstituted benzoic acids, for example 4-t-butylphenyl salicylate, phenyl salicylate, octylphenyl salicylate, dibenzoylresorcinol, bis(4-t-butylbenzoyl)resorcinol, benzoylresorcinol, 2,4-di-t-butylphenyl 3,5-di-t-butyl-4-hydroxybenzoate, hexadecyl 3,5-di-t-butyl-4-hydroxybenzoate, octadecyl 3,5-di-t-butyl-4-hydroxybenzoate, 2-methyl-4,6-di-t-butylphenyl 3,5-di-t-butyl-4-hydroxybenzoate.

2.4 Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(α-carbomethoxy-β-cyanovinyl)-2-methylindoline.

2.5 Nickel compounds, for example nickel complexes of 2,2-thiobis[4-(1,1,3,3-tetramethylbutyl)phenol], such as the 1:1 or 1=2 complex, with or without additional ligands such as n-butylamine, triethanolamine or N-cyclohexyldiethanolamine, nickel dibutyldithiocarbamate, nickel salts of the monoalkyl esters, such as the methyl or ethyl ester, of 4-hydroxy-3,5-di-t-butylbenzyl-phosphonic acid, nickel complexes of ketoximes, such as of 2-hydroxy-4-methylphenyl undecylketoxime, nickel complexes of 1-phenyl-4-lauroyl-5-hydroxypyrazole, with or without additional ligands.

2.6 Sterically hindered amines, for example bis(2,2,6,6-tetramethylpiperidyl) sebacate, bis(2,2,6,6-tetramethylpiperidyl) glutarate, bis(2,2,6,6-tetramethylpiperidyl) succinate, bis(1,2,2,6,6-pentamethylpiperidyl) sebacate, bis(1,2,2,6,6-pentamethylpiperidyl) glutarate, bis(1,2,2,6,6-pentamethylpiperidyl ) n -butyl -3,5-di-t-butyl-4-hydroxybenzylmalonate, 2,2,6,6- tetramethylpiperidyl behenate, 1,2,2,6,6-pentamethylpiperidyl behenate, the condensate of 1-hydroxyethyl-2,2,6,6-tetramethyl-4 hydroxypiperidine and succinic acid, the condensate of N,N'-bis(2,2, 6,6- tetramethyl-4-piperidyl)hexamethylenediamine and 4-t-octylamino-2,6-dichloro-1,3,5-s-triazine, tris(2,2,6,6-tetramethyl-4-piperidyl) nitrilotriacetate, tetrakis (2,2,6,6-tetramethyl-4-piperidyl) 2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, 4-stearyloxy-2,2,6,6-tetramethylpiperidine, 4-stearyloxy-1,2,2,6,6-pentamethylpiperidine, 4-stearyloxy-1,2,2,6,6-pentamethylpiperidine, bis( 1,2,2,6,6-pentamethylpiperidyl)-2-n-butyl-2-(2-hydroxy-3,5-di-t-butylbenzyl) malonate, bis(1,2,2,6,6-pentamethylpiperidyl)

2-n-butyl-2-(-4-hydroxy-3,5-di-t-butylbenzyl)malonate, 3-n-octyl- 7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl) -1,3,5-triazine and 1,2-bis(3-aminopropylamino) ethane, the condensate of 2-chloro-4,6-di(4-methoxypropylamino-2,2,6,6-tetramethylpiperidyl) -1,3,5-triazine and 1,2bis(3-aminopropylamino)ethane, the condensate of 2chloro-4,6-di(4-methoxypropylamino-1,2,2,6,6-pentamethyl-piperidyl)-1,3,5-triazine and 1,2-bis(3-aminopropylamino) ethane, the condensate of 2-chloro-4,6-di( 4-n-butylamino-1,2,2,6,6-pentamethylpiperidyl)-1,3,5-triazine and 1,2-bis(3-aminopropylamino)ethane, the products of the reaction of 2-chloro-4,6-di(4-n-butylamino-2,2,6,6-tetramethylpiperidyl)-1,3,5-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino)ethane, the products of the reaction of 2-chloro-4,6-di(4-n-butylamino1,2,2,6,6-pentamethylpiperidyl)-1,3,5- triazine with mono or polyamines, where between one and all the active H atoms on the amine are replaced, such as with ethylenediamine, diethylenetriamine, triethylenetetramine, hexamethylenediamine or 1,2-bis(3- aminopropylamino)-ethane, the products of the reaction of 2-chloro- 4,6-di(4-n-butylamino-2,2,6,6-tetramethylpiperidyl)- 1,3,5-triazine and 4-t-octylamino-2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino) ethane, the products of the reaction of 2-chloro-4,6-di (4-n-butylamino-1,2,2,6,6-pentamethylpiperidyl)-1,3,5-triazine and 4-t-octylamino-2,6-dichloro-1,3,5-s-triazine with mono- or polyamines, where between one and all the active. H atoms on the amine are replaced, such as with ethylenediamine, diethylenetriamine, triethylenetetramine, hexamethylenediamine or 1,2-bis(3-aminopropylamino) ethane, the products of the reaction of 2-chloro-4,6-di(4-n-butylamino-2,2,6,6-tetramethylpiperidyl)-1,3,5-triazine and 4-(4-n-butylamino-2,2,6,6-tetramethylpiperidyl)-2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3,aminopropylamino) ethane, the products of the reaction of 2-chloro-4,6-di( 4-n-butyl-amino-1,2,2,6,6-pentamethylpiperidyl)-1,3,5-triazine and 4-(4-n-butylamino-2,2,6,6-tetramethylpiperidyl)-2,6-dichloro-1,3,5-s-triazine with mono- or polyamines, where between one and all the active H atoms on the amine are replaced, such as with ethylenediamine, diethylenetriamine, triethylenetetramine, hexamethylenediamine or 1,2-bis(3-aminopropylamino)ethane, 3-dodecyl- 7,7,9,9-tetramethyl-1,3,8-triazaspiro[4,5]decane-2,4-dione, oligomerized 2,2,4,4-tetramethyl-20-(oxiranylmethyl)- 7-oxa-3,2 0-diazadispiro [5.1.11.2]heneicosan-21-one, oligomerized 1,2,2,4, 4-pentamethyl -20-(oxiranylmethyl)- 7-oxa-3,2 0-diazadispiro [5.1.11.2]heneicosan-21-one, oligomerized 1-acetyl-2,2,4,4-tetramethyl- 20-(oxiranylmethyl)-7-oxa-3,20-diazadispiro[5.1.11.2]heneicosan-21-one, dodecyl-1-(2,2,4, 4-tetramethyl- 4-piperidyl)-pyrrolidine-2,5-dione, 3-dodecyl-1-( 1,2,2,6,6-penta-methyl-4-piperidyl)pyrrolidine-2,5-dione, 2,2,4,4-tetra-methyl-7-oxa-3,20-diazadispiro[5.1.11.2]heneicosan-21-one, dodecyl 2,2,4,4-tetramethyl-7-oxa-21-oxo-3,20diazadispiro[5.1.11.2]heneicosane-3-propanoate, tetradecyl 2,2,4,4-tetramethyl-7-oxa-21-oxo-3,20-diazadispiro[5.1.11.2]heneicosane-3-propanoate, 2,2,3,4,4-penta-methyl-7-oxa-3,20-diazadispiro[5.1.11.2] heneicosan-21-one, dodecyl 2,2,3,4,4-pentamethyl-7-oxa-21-oxo-3,20diazadispiro[5.1.11.2]heneicosane-3-propanoate, tetradecyl 2,2,3,4,4-pentamethyl-7-oxa-21-oxo-3,20-diazadispiro[5.1.11.2]heneicosane-3-propanoate, 3-acetyl2,2,4,4-tetramethyl-7-oxa-3,20-diazadispiro [5.1.11.2 ]-heneicosan-21-one, dodecyl 3-acetyl-2,2,4,4-tetramethyl-7-oxa-21-oxo-3,20-diazadispiro[5.1.11.2]heneicosane-3propanoate, tetradecyl 3-acetyl-2,2,4,4-tetramethyl- 7-oxa-21-oxo-3,20-diazadispiro[5.1.11.2] heneicosane-3propanoate, 1,1',3,3',5,5'-hexahydro-2,2',4,4', 6,6'-hexaaza-2,2'6 6'-bismethano- 7,8-dioxo-4,4'-bis-(1,2,2, 6,6-pentamethyl-4-piperidyl)biphenyl, poly-N,N'-bis (2,2,6, 6-tetramethyl -4-piperidyl)-1,8-diazadecylene, the addition compound of 2,2,6,6-tetramethyl-4-allyloxypiperidine and polymethylhydrosiloxane (molecular weight up to 4000), the addition compound of 1,2,2,6,6-pentamethyl-4-allyloxypiperidine and polymethylhydrosiloxane (molecular weight up to 4000), N,N'-diformyl-N,N'-bis-(2,2,6,6- tetramethyl-4-piperidyl) hexamethylenediamine, N,N'-di formyl-N,N'-bis(1,2,2,6,6-pentamethyl -4 piperidyl)hexamethylenediamine, 5,11-bis(2,2,6,6-tetramethyl-4-piperidyl) -3,5,7,9,11,13-hexaazatetracyclo[[7.4.0.0$^{2,7}$.1$^{3,13}$]tetradecane-8,14-dione, 5,11-bis(1,2,2,6,6-pentamethyl -4-piperidyl) -3,5,7,9,11,13-hexaazatetracyclo [7.4.0.0$^{2,7}$1.$^{3,}$ 13]tetradecane-8,14-dione, 7,7,9,9- tetramethyl -8-acetyl -3-dodecyl -1,3,8- triazaspiro[4.5]decane-2,4-dione, bis(2,2, 6,6- tetramethyl-4 piperidyl) [(4-methoxyphenyl ) methylene]propanedioate, bis (1,2,2,6,6-pentamethyl-4-piperidyl) [(4-methoxyphenyl) methylene]propanedioate, 2,4,6-tris(N-cyclohexyl-N- [2-(3,3,4,5,5-pentamethylpiperazinon-1-yl) ethyl]amino) 1,3,5-triazine, copolymer of styrene with α-methylstyrene and maleic anhydride reacted with 4-amino-2,2,6,6-tetramethylpiperidine and octadecylamine, copolymer of styrene with α-methylstyrene and maleic anhydride reacted with 4-amino-1,2,2,6,6-pentamethylpiperidine and octadecyl amine, polycarbonate with 2,2'-[(2,2, 6,6-tetramethyl-4piperidyl)imino]bisethanol as diol component, polycarbonate with 2,2'- [(1,2,2,6,6-pentamethyl-4piperidyl)imino]bisethanol as diol component, copolymer of maleic anhydride and an α-olefin having up to 30 carbon atoms reacted with 4-amino-2,2,6,6-tetramethylpiperidine, copolymer of maleic anhydride and an α-olefin having up to 30 carbon atoms reacted with 1-acetyl- 4-amino-2,2,6,6-tetramethylpiperidine, copolymer of maleic anhydride and an α-olefin having up to 30 carbon atoms reacted with 4-amino-1,2,2,6,6-pentamethylpiperidine, and the N-alkyl- and N-aryloxy derivatives of the abovementioned compounds containing free NH groups on the piperidine, specifically α-methylbenzoxy and $C_1$ to $C_{18}$-alkoxy.

2.7 Oxalamides, for example 4,4'-dioctyloxyoxanilide, 2,2,-dioctyloxy-5,5'-di-t-butoxanilide, 2,2 '-didodecyloxy-5, 5'-di-t-butoxanilide, 2-ethoxy-2'-ethoxanilide, N,N'-bis(3-dimethylaminopropyl)oxalamide, 2-ethoxy- 5-t-butyl-2'-ethoxanilide and its mixture with 2-ethoxy- 2'-ethyl-5,4'-di-t-butoxanilide and mixtures of ortho- and paramethoxy and of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy -4-octyloxyphenyl)-4,6-bis(2,4-dimethylphenyl)-1, 3,5-triazine, 2-(2,4-dihydroxyphenyl)-4,6-bis( 2,4 dimethylphenyl)-1,3,5-triazine, 2,4-bis(2-hydroxy- 4-propyloxyphenyl)-6-(2,4-dimethylphenyl)-1,3,5-triazine, 2-(2- hydroxy-4-octyloxyphenyl)-4,6-bis(4-methylphenyl)-1,3,5-triazine, 2-(2-hydroxy-4-dodecyloxyphenyl)- 4,6bis(2,4-dimethylphenyl)-1,3,5-triazine, 2-[2-hydroxy-4-(2-hydroxy-3-butyloxy-propoxy) phenyl]-4,6-bis(2,4-dimethylphenyl)-1,3,5-triazine, 2-[2-hydroxy-4-(2-hydroxy-3-octyloxy-propoxy)phenyl]-4,6-bis(2,4-dimethylphenyl)-1,3,5-triazine, 3 Metal deactivators, for example N,N'-diphenyloxamide, N-salicylal-N'-salicyloyl-hydrazine, N,N'-bis(salicyloyl)hydrazine, N,N'-bis (3,5-di-t-butyl- 4-hydroxyphenyl-propionyl)hydrazine, 3-salicyloylamino-1,2,4-triazole, bis(benzylidene) oxalyl dihydrazide, oxanilide, isophthaloyl dihydrazide, sebacoyl bisphenylhydrazide, N,N'-diacetyladipodihydrazide, N,N'-bis(salicyloyl) oxalyl dihydrazide, N,N'-bis(salicyloyl) thiopropionyl dihydrazide.

4 Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-t-butylphenyl) phosphite, diisodecyl pentaerythritol diphosphite, bis(2,4-di-t-butylphenyl) pentaerythritol diphosphite, bis(2,6-di-t-butyl-4-methylphenyl)-pentaerythritol diphosphite, bis-isodecyloxypentaerythritol diphosphite, bis(2,4-di-t-butyl-6-methylphenyl)-pentaerythritol diphosphite, bis(2,4,6-tri-t-butylphenyl)-pentaerythritol diphosphite, tristearyl sorbitol triphosphite, tetrakis-(2,4-di-t-butylphenyl) 4,4'-biphenylene diphosphonite, 6-isooctyloxy-2,4,8,10-tetra-t-butyl-12H-dibenzo[d, g]-1,3,2-dioxaphosphocine, 6-fluoro-2,4,8,10-tetra-t-butyl-12-methyl-dibenzo [d, g]-1,3,2-dioxaphosphocine, bis(2,4-di-t-butyl-6-methylphenyl) methyl phosphite, bis(2,4-di-t-buryl-6-methylphenyl) ethyl phosphite, tris(2-t-butyl-4-thio(2'-methenyl-4'-hydroxy -5'-t-butyl)phenyl -5-methenyl) phenyl phosphite.

5 Peroxide scavengers, for example esters of β-thiodipropionic acid, for example the lauryl stearyl, myristyl or tridecyl esters, mercaptobenzimidazole or the zinc salt of 2-mercaptobenzimidazole, zinc alkyldithiocarbamates, zinc dibutyldithiocarbamate, dioctadecyl monosulfide, dioctadecyl disulfide, pentaerythritol tetrakis(β-dodecylmercapto)propionate.

6 Polyamide stabilizers, for example copper salts in combination with iodides and/or phosphorus compounds and salts of divalent manganese.

7 Basic costabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or tin pyrocatecholate.

8 Nucleating agents, for example 4-t-butylbenzoic acid, adipic acid, diphenylacetic acid.

9 Fillers and reinforcing agents, for example calcium carbonate, silicates, glass fibers, asbestos, talc, kaolin, mica, barium sulfate, metal oxides and hydroxides, carbon black and graphite.

10 Other additives, for example plasticizers, lubricants, emulsifiers, pigments, optical brighteners, flameproofing agents, antistatic agents and blowing agents.

The additives are incorporated into the organic polymers by generally conventional methods. For example, the incorporation can be effected by mixing or applying the compounds and, if desired, further additives into or onto the polymer directly after the polymerization or into the melt before or during the shaping. The incorporation can also be carried out by applying the dissolved or dispersed compounds to the polymer directly or by mixing into a solution, suspension or emulsion of the polymer, if necessary subsequently allowing the solvent to evaporate. The compounds are also effective if they are subsequently introduced into a pre-granulated polymer in a separate processing step.

The compounds used in accordance with the invention can also be added to the polymers to be stabilized in the form of a masterbatch containing these compounds, for example, in a concentration of from 1 to 75% by weight, preferably from 2.5 to 30% by weight.

The novel compounds are excellent light stabilizers which are distinguished by low volatility.

The examples below are intended to illustrate the invention in greater detail.

EXAMPLE 1

15.7 g of 20,20'-(2-hydroxy-1, 3-propanediyl)bis[2,2,4,4-tetramethyl-7-oxa-3,20-diazadispiro[5.1.11.2]heneicosan21-one]were introduced into 80 cm$^3$ of xylene together with 2.2 g of triethylamine. 2.8 g of 2-chloro-1,3,2-dioxaphospholane were added at room temperature and the mixture was subsequently refluxed for 5 hours. Water was then added to the batch, and the aqueous phase was rendered alkaline and washed by shaking several times with xylene. After drying using magnesium sulfate and evaporation of the solution, the resin which remained was recrystallized from ethanol, giving 11.4 g of a white product having a melting point of 128° C.

EXAMPLE 2

16.2 g of 20,20'-(2-hydroxy-1,3-propanediyl)bis[2,2,3,4,4-pentamethyl-7-oxa-3,20-diazadispiro[5.1.11.2 ]-heneicosan-21-one]and 2.2 g of triethylamine were introduced into 80 cm$^3$ of toluene. A solution of 2.8 g of 2-chloro-1,3,2-dioxaphospholane in 20 cm$^3$ of toluene was slowly added dropwise with stirring at room temperature; the batch was subsequently refluxed for 5 hours. For work-up, the mixture was poured into water, the phases were separated, the aqueous phase was extracted twice with ethyl acetate, and the combined organic phases were dried. Evaporation gave 16.2 g of pale yellow, non-crystallizing resin.

EXAMPLE 3

9.2 g of 20,20'-(2-hydroxy-1,3-propanediyl)bis[2,2,4,4-tetramethyl-7-oxa-3,20-diazadispiro[5.1.11.2]heneicosan-1-one]and 5.1 g of triethylamine were introduced into 100 cm$^3$ of toluene. 5.4 g of chlorotrimethylsilane were slowly added dropwise at room temperature, and the mixture was subsequently heated at 50° C. for 8 hours. The batch was washed by shaking with water, and the organic phase was dried using sodium sulfate. On cooling, 23.4 g of product crystallized as a white solid having a melting point of 187° C.

EXAMPLE 4

0.5 g of sodium hydride were introduced into 50 cm$^3$ of methyl t-butyl ether, and a solution of 16.2 g of 20,20'-(2-hydroxy-1, 3-propanediyl)bis[2,3,4,4-pentamethyl-7-oxa-3, 20-diazadispiro[5.1.11.2]heneicosan- 21-one] in 100 cm$^3$ of methyl t-butyl ether was slowly added dropwise at room temperature. After i hour, 2.4 g of trimethylchlorosilane in 50 cm$^3$ of methyl t-butyl ether were likewise added dropwise at room temperature, and the batch was stirred for 20 hours. Finally, the mixture was refluxed for 3 hours. Excess sodium hydride was destroyed using a little methanol, and the batch was poured into water. The organic phase was separated off, washed by shaking with water and dried using sodium sulfate. Evaporation of the solution left 13.5 g of the target compound as a colorless, glassy material.

EXAMPLE 5

3.2 g of dichlorodimethylsilane were added dropwise to a solution of 5.1 g of triethylamine and 39.2 g of 20,20'-(2-hydroxy-1, 3-propanediyl)bis[2,2,4,4-tetramethyl-7-oxa-3, 20-diazadispiro[5.1.11.2]heneicosan-21-one] in xylene. The mixture was subsequently heated at 50° C. for 12 hours. The batch was washed by shaking with water, and the organic phase was dried and evaporated. The oil remaining could be recrystallized from acetone, giving 41.1 g of a white solid having a melting point of 161° C.

EXAMPLE 6

A solution of 16.2 g of 20,20'-(2-hydroxy- 1,3-propanediyl)bis [2,2,3,4,4-pentamethyl-7-oxa-3,20-diazadispiro[5.1.11.2]heneicosan-21-one] in 100 cm³ of methyl t-butyl ether was added dropwise to a suspension of 0.5 g of sodium hydride in 50 cm³ of methyl t-butyl ether, and the mixture was stirred for 1 hour. 1.3 g of dichlorodimethylsilane were subsequently added dropwise, and the mixture was refluxed for a further 12 hours. Sodium hydride remaining was then destroyed using a little methanol, and the batch was washed several times by shaking with water. Drying and evaporation of the organic phase left 13.3 g of the target compound as a pale yellow, resinous material.

EXAMPLE 7

2.2 g of methyl chloroformate were added to 15.7 g of 2 0,2 0'-(2-hydroxy-1,3-propanediyl) bis [2,2,4,4- tetramethyl-7-oxa -3,20-diazadispiro[5.1.11.2 ]heneicosan-21 one-] and 2.2 g of triethylamine in 80 cm³ of xylene, and the mixture was refluxed for 5 hours. The batch was then washed several times by shaking with water, and the organic phase was dried and evaporated. The resin remaining could be recrystallized from acetone, giving 13.6 g of colorless crystals.

EXAMPLE 8

14 cm³ of a 1.6 molar butyllithium solution, diluted with 20 cm³ of toluene, were added dropwise at room temperature to a solution of 16.2 g of 20,20'-(2-hydroxy-1,3-propanediyl)bis[2,2,3,4,4-pentamethyl-7-oxa-3,20-diazadispiro [5.1.11.2]heneicosan-21-one] in 60 cm³ of toluene. After 1 hour, a solution of 2.1 g of methyl chloroformate in 20 cm³ of toluene was added dropwise, and the batch was stirred at room temperature for 20 hours. For work-up, the mixture was poured into water, and the organic phase was separated off and dried using sodium sulfate. Evaporation of the solution gave 14.2 g of the target compound as a colorless, glassy material.

EXAMPLE 9

16.2 g of 20,20'- (2-hydroxy-1,3-propanediyl)bis-[2,2,3, 4,4-pentamethyl-7-oxa-3,20-diazadispiro [5.1.11.2 ]-heneicosan-21-one] and 2.8 g of potassium carbonate were introduced into 80 cm³ of toluene. 9.1 g of 2-chloro- 4,6-bis [1,2,2,6,6-pentamethyl-4-piperidinyloxy]-1,3,5-triazine were added, and the mixture was refluxed for 5 hours. The cooled mixture was diluted with 100 cm³ of toluene and washed four times by shaking with water. Drying and removal of the solvent by distillation left 21.2 g of a colorless, glassy material.

EXAMPLE 10

The volatility of novel compounds was determined in a thermogravimetric analysis apparatus. To this end, equal amounts (500 mg) of the novel compounds were heated to 300° C. in a nitrogen atmosphere at a heating rate of 2K/min, and the loss of substance was measured in mg/cm² of sample surface. The results are shown in the Table below:

| Compound from Example | Weight loss in mg/cm² on reaching . . . °C. | | | |
| --- | --- | --- | --- | --- |
|  | 220 | 260 | 300 | 10 min at 300° C. |
| 3 | 0.0 | 0.2 | 0.8 | 2.0 |
| 4 | 0.3 | 0.3 | 0.7 | 1.2 |
| 5 | 1.7 | 2.0 | 2.3 | 2.7 |
| 8 | 0.2 | 1.9 | 3.2 | 3.8 |
| Comp.[1]: 14 | 0.6 | 2.5 | 7.7 | 12.6 |
| Comp.[1]: 15 | 1.4 | 3.9 | 8.1 | 13.3 |

Comp.[1]: from EP 57 885

We claim:

1. A polyalkylpiperidine compound of the formula I

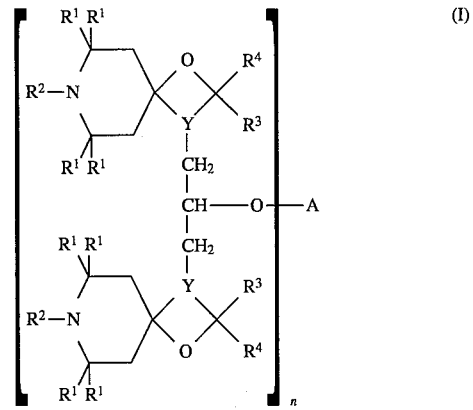

in which Y is a group

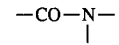

$R^1$ is a hydrogen atom or a $C_{1-20}$ alkyl group, $R^2$ is a hydrogen atom or a $C_{1-20}$ alkyl group, $R^3$ and $R^4$ are identical or different and are a hydrogen atom or a $C_{1-20}$ alkyl group, or $R^3$ and $R^4$, together with the carbon atom connecting them, form a ring having 5 to 12 ring members, n is 1, 2 or 3, and A, in the case n=1, is —COOR⁵, —P(OR⁶) (OR⁷), —Si(OR⁵) (OR⁵), —SiR⁵R⁵R⁵ or the

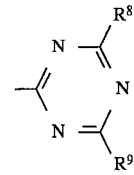

group,

A, in the case where n=2, is —CO—, =POR$^5$, =Si(OR$^5$)(OR$^5$), =SiR$^5$R$^5$ or the

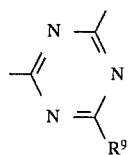

group,

A, in the case where n=3, is ≡Si(OR$^5$), ≡SiR$^5$ or the

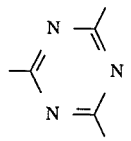

group,

R$^5$ is a C$_1$–C$_{18}$-alkyl group, a C$_2$–C$_{18}$-alkenyl group, a C$_2$–C$_{18}$alkynyl group, a C$_5$–C$_{12}$cycloalkyl group, a C$_6$–C$_{10}$-bicycloalkyl group, a C$_5$–C$_8$-cycloalkenyl group, a C$_6$–C$_{10}$-aryl group, a C$_7$–C$_9$aralkyl group, a C$_7$–C$_9$-alkaryl group, unsubstituted or substituted by C$_1$–C$_4$-alkyl or phenyl, where a plurality of radicals R$^5$ may be identical or different, R$^6$ and R$^7$ are identical or different and are a C$_1$–C$_{18}$-alkyl group, a C$_2$–C$_{18}$ alkenyl group, a C$_2$–C$_{18}$-alkynyl group, a C$_5$–C$_{12}$ cycloalkyl group, a C$_6$–C$_{10}$-bicycloalkyl group, a C$_5$–C$_8$-cycloalkenyl group, a C$_6$–C$_{10}$-aryl group, a C$_7$–C$_9$-aralkyl group or a C$_7$–C$_9$-aralkyl group, substituted by C$_1$–C$_4$-alkyl or phenyl, or R$^6$ and R$^7$ together are a radical of the formula II or III

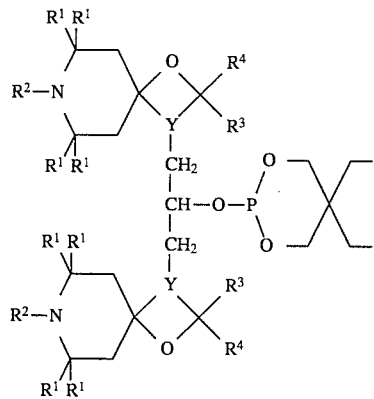

(II)

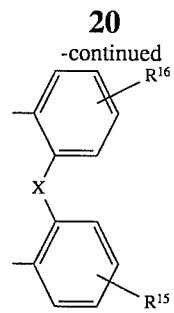

(III)

in which R$^1$, R$^2$, R$^3$, R$^4$ and R$^5$ are as defined above, and X is a direct bond or methylene group or a 1,1-alkylidene group having 2 to 5 carbon atoms, R$^8$ and R$^9$ are identical or different and are —OR$^5$, —NHR$^5$, —NR$^{11}$R$^{12}$ or one of the two groups of the formula

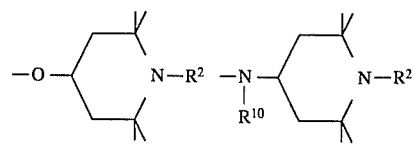

which R$^{10}$ is a hydrogen atom, a C$_1$–C$_{12}$-alkyl group, a C$_5$–C$_7$-cycloalkyl group, a C$_7$–C$_9$-aralkyl group, a C$_8$–C$_{18}$-alkanoyl group, a C$_3$–C$_5$-alkenoyl group or a benzoyl group, or in which R$^{10}$ is

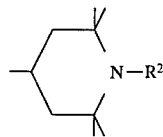

R$^{11}$ and R$^{12}$ are identical or different and are a C$_1$–C$_{10}$-alkyl group, a C$_5$–C$_7$-cycloalkyl group or a C$_6$–C$_{10}$-aryl group, or R$^{11}$ and R$^{12}$, together with the nitrogen, form a 5- to 12-membered ring, which may also contain oxygen.

2. A compound as claimed in claim 1, wherein R$^1$ in the formula I is a methyl group.

3. A compound as claimed in claim 1, wherein R$^2$ in the formula I is a methyl group.

* * * * *